(12) United States Patent
Nguyen et al.

(10) Patent No.: US 8,940,358 B2
(45) Date of Patent: Jan. 27, 2015

(54) MAINTAINING A FIXED DISTANCE BY LASER OR SONAR ASSISTED POSITIONING DURING COATING OF A MEDICAL DEVICE

(75) Inventors: Binh Nguyen, Newark, CA (US); Randy Shen, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 251 days.

(21) Appl. No.: 13/158,057

(22) Filed: Jun. 10, 2011

(65) Prior Publication Data

US 2012/0315374 A1    Dec. 13, 2012

(51) Int. Cl.
*A61M 25/00*    (2006.01)
*A61M 25/10*    (2013.01)
*B05B 13/04*    (2006.01)
*B05C 5/00*    (2006.01)

(52) U.S. Cl.
CPC ........ *A61M 25/1029* (2013.01); *B05B 13/0442* (2013.01); *B05C 5/00* (2013.01); *A61M 2025/1031* (2013.01); *A61M 2025/105* (2013.01)
USPC .......................... 427/2.28; 427/2.25; 427/2.24

(58) Field of Classification Search
USPC ................................. 427/421, 2.24
See application file for complete search history.

(56) References Cited

U.S. PATENT DOCUMENTS

| | | |
|---|---|---|
| 4,743,465 A | 5/1988 | Saeki et al. |
| 4,748,982 A | 6/1988 | Horzewski et al. |
| 5,300,085 A | 4/1994 | Yock |
| 5,370,614 A | 12/1994 | Amundson et al. |
| 5,464,650 A | 11/1995 | Berg et al. |
| 5,496,346 A | 3/1996 | Horzewski et al. |
| 5,591,227 A | 1/1997 | Dinh et al. |
| 5,626,600 A | 5/1997 | Horzewski et al. |
| 5,649,977 A | 7/1997 | Campbell |
| 5,911,452 A | 6/1999 | Yan |
| 5,980,972 A | 11/1999 | Ding |
| 6,120,847 A | 9/2000 | Yang et al. |
| 6,406,457 B1 | 6/2002 | Wang et al. |
| 6,478,807 B1 | 11/2002 | Foreman et al. |
| 6,494,906 B1 | 12/2002 | Owens |
| 6,669,980 B2 | 12/2003 | Hansen |
| 6,676,987 B2 | 1/2004 | Zhong et al. |
| 6,743,462 B1 | 6/2004 | Pacetti |

(Continued)

OTHER PUBLICATIONS

Vivekanandhan et al., COmputer Aided Torch Trajectory Generation for Automated Coating of PArts with Complex Surfaces, 1994, Journal of Thermal Spray Technology, vol. 3 (2), 208-215.*

(Continued)

*Primary Examiner* — Dah-Wei D Yuan
*Assistant Examiner* — Andrew Bowman
(74) *Attorney, Agent, or Firm* — Baker Botts LLP

(57) ABSTRACT

System and method for coating an expandable member of a medical device comprising a support structure to support the expandable member and an applicator positioned with at least one outlet proximate a surface of an expandable member. A drive assembly establishes relative movement between the at least one outlet and the surface of the expandable member to apply fluid on the surface of the expandable member along a coating path. A positioning device is provided to determine the distance to the surface of the expandable member at a corresponding location and relays the information to a controller or the like to maintain a substantially fixed distance between the outlet of the applicator and the surface of the expandable member when in alignment with the corresponding location.

24 Claims, 5 Drawing Sheets

(56) References Cited

U.S. PATENT DOCUMENTS

| | | | |
|---|---|---|---|
| 7,241,344 | B2 | 7/2007 | Worsham et al. |
| 7,335,227 | B2 | 2/2008 | Jalisi |
| 7,378,105 | B2 | 5/2008 | Burke et al. |
| 7,445,792 | B2 | 11/2008 | Toner et al. |
| 7,455,876 | B2 | 11/2008 | Castro et al. |
| 7,504,125 | B1 | 3/2009 | Pacetti et al. |
| 7,524,527 | B2 | 4/2009 | Stenzel |
| 2001/0021419 | A1 | 9/2001 | Luthje et al. |
| 2004/0062875 | A1* | 4/2004 | Chappa et al. ............ 427/421 |
| 2004/0073284 | A1 | 4/2004 | Bates et al. |
| 2004/0234748 | A1 | 11/2004 | Stenzel |
| 2005/0158449 | A1 | 7/2005 | Chappa |
| 2005/0196518 | A1 | 9/2005 | Stenzel |
| 2007/0031611 | A1 | 2/2007 | Babaev |
| 2007/0088255 | A1 | 4/2007 | Toner et al. |
| 2007/0179591 | A1 | 8/2007 | Baker et al. |
| 2008/0113081 | A1 | 5/2008 | Hossainy et al. |
| 2009/0226598 | A1 | 9/2009 | Feng et al. |
| 2010/0023108 | A1 | 1/2010 | Toner et al. |
| 2010/0030183 | A1 | 2/2010 | Toner et al. |
| 2010/0040766 | A1 | 2/2010 | Chappa et al. |
| 2010/0055294 | A1 | 3/2010 | Wang et al. |
| 2011/0151199 | A1 | 6/2011 | Nelson et al. |
| 2011/0281019 | A1 | 11/2011 | Gong et al. |
| 2011/0281020 | A1 | 11/2011 | Gong et al. |
| 2012/0022540 | A1 | 1/2012 | Chasmawala et al. |
| 2012/0064223 | A1 | 3/2012 | Gamez et al. |
| 2012/0065583 | A1 | 3/2012 | Serna et al. |
| 2012/0128863 | A1 | 5/2012 | Nguyen et al. |
| 2012/0143054 | A1 | 6/2012 | Eaton et al. |
| 2012/0315375 | A1 | 12/2012 | Shen et al. |
| 2012/0315376 | A1 | 12/2012 | Nguyen et al. |
| 2014/0113059 | A1 | 4/2014 | Shen et al. |

OTHER PUBLICATIONS

Cornell, Maintaining Distance Using Sonar video, Youtube, 2010, www.youtube.com/watch?v=pj6jxo2sqgw.*
U.S. Appl. No. 12/882,990, filed Sep. 15, 2010.
U.S. Appl. No. 13/158,101, filed Jun. 10, 2011.
U.S. Appl. No. 13/158,131, filed Jun. 10, 2011.
Unverdoben, Martin, "The Paclitaxel-Eluting PTCA-Balloon Catheter in Coronary Artery Disease PEPCAD I-SVD PEPCAD II-ISR",Clinical Research Institute, Center for Cardiovascular Diseases, 2005-2006, Rotenburg/Fulda, Germany.
U.S. Appl. No. 12/882,953, filed Sep. 15, 2010.
U.S. Appl. No. 13/280,067, filed Oct. 24, 2011.
U.S. Appl. No. 12/882,990, Apr. 8, 2013 Response to Non-Final Office Action.
U.S. Appl. No. 13/108,283, Mar. 28, 2013 Non-Final Office Action.
U.S. Appl. No. 12/882,953, Apr. 12, 2013 Response to Non-Final Office Action.
U.S. Appl. No. 12/882,953, Jan. 15, 2013 Non-Final Office Action.
U.S. Appl. No. 12/882,990, Dec. 6, 2012 Non-Final Office Action.
U.S. Appl. No. 13/280,067, Apr. 26, 2013 Applicant Summary of Interview with Examiner.
U.S. Appl. No. 13/158,101, Apr. 26, 2013 Restriction Requirement.
U.S. Appl. No. 13/109,156, Apr. 26, 2013 Restriction Requirement.
U.S. Appl. No. 13/109,156, Sep. 10, 2013 Non-Final Office Action.
U.S. Appl. No. 12/882,953, Dec. 9, 2013 Notice of Allowance.
U.S. Appl. No. 12/882,953, Nov. 15, 2013 Request for Continued Examination (RCE).
U.S. Appl. No. 12/882,953, filed Oct. 28, 2013 Advisory Action.
U.S. Appl. No. 12/882,953, Oct. 16, 2013 Response to Final Office Action.
U.S. Appl. No. 12/882,953, Aug. 16, 2013 Final Office Action.
U.S. Appl. No. 13/158,101, Oct. 7, 2013 Notice of Allowance.
U.S. Appl. No. 13/158,101, Sep. 17, 2013 Supplemental Amendment and Statement of the Substance of the Interview.
U.S. Appl. No. 13/108,283, Nov. 12, 2013 Issue Fee payment.
U.S. Appl. No. 13/108,283, Aug. 12, 2013 Notice of Allowance.
U.S. Appl. No. 12/882,990, Oct. 11, 2013 Advisory Action.
U.S. Appl. No. 12/882,990, Oct. 1, 2013 Response to Final Office Action.
U.S. Appl. No. 12/882,990, Aug. 1, 2013 Final Office Action.
PlumbingSupply.com, "Pipe Hangers and Brackets", (Feb. 2001), www.plumbingsupply.com/pipehangers.htlm.
U.S. Appl. No. 14/078,212, filed Nov. 12, 2013.
U.S. Appl. No. 12/882,953, Mar. 7, 2014 Issue Fee payment.
U.S. Appl. No. 12/882,990, Dec. 19, 2013 Non-Final Office Action.
U.S. Appl. No. 13/158,131, Mar. 13, 2014 Non-Final Office Action.
U.S. Appl. No. 13/109,156, Mar. 20, 2014 Response to Final Office Action.
U.S. Appl. No. 14/078,212, Jun. 6, 2014 Non-Final Office Action.

* cited by examiner

MAINTAINING A FIXED DISTANCE BY LASER OR SONAR ASSISTED POSITIONING DURING COATING OF A MEDICAL DEVICE

BACKGROUND OF THE DISCLOSED SUBJECT MATTER

1. Field of the Disclosed Subject Matter

The presently disclosed subject matter is related to the delivery of a therapeutic agent from an interventional medical device. Particularly, the disclosed subject matter relates to the method and system for maintaining a fixed distance between an outlet of an applicator and the surface of an expandable member during application of one or more therapeutic agents.

2. Description of Related Subject Matter

Atherosclerosis is a disease affecting arterial blood vessels. It is characterized by a chronic inflammatory response in the walls of arteries, which is in large part due to the accumulation of lipid, macrophages, foam cells and the formation of plaque in the arterial wall. Atherosclerosis is commonly referred to as hardening of the arteries, although the pathophysiology of the disease manifests itself with several different types lesions ranging from fibrotic to lipid laden to calcific. Angioplasty is a vascular interventional technique involving mechanically widening an obstructed blood vessel, typically caused by atherosclerosis.

During angioplasty, a catheter having a folded balloon is inserted into the vasculature of the patient and is passed to the narrowed location of the blood vessel at which point the balloon is inflated to the desired size by fluid pressure. Percutaneous coronary intervention (PCI), commonly known as coronary angioplasty, is a therapeutic procedure to treat the stenotic regions in the coronary arteries of the heart, often found in coronary heart disease. In contrast, peripheral angioplasty, commonly known as percutaneous transluminal angioplasty (PTA), generally refers to the use of mechanical widening of blood vessels other than the coronary arteries. PTA is most commonly used to treat narrowing of the leg arteries, especially, the iliac, external iliac, superficial femoral and popliteal arteries. PTA can also treat narrowing of carotid and renal arteries, veins, and other blood vessels.

Although the blood vessel is often successfully widened by angioplasty, sometimes the treated region of the blood vessel undergoes vasospasm, or abrupt closure after balloon inflation or dilatation, causing the blood vessel to collapse after the balloon is deflated or shortly thereafter. One solution to such collapse is stenting the blood vessel to prevent collapse. A stent is a device, typically a metal tube or scaffold that is inserted into the blood vessel after, or concurrently with angioplasty, to hold the blood vessel open.

While the advent of stents eliminated many of the complications of abrupt vessel closure after angioplasty procedures, within about six months of stenting a re-narrowing of the blood vessel can form, a condition known as restenosis. Restenosis was discovered to be a response to the injury of the angioplasty procedure and is characterized by a growth of smooth muscle cells and extracellular matrix—analogous to a scar forming over an injury. To address this condition, drug eluting stents were developed to reduce the reoccurrence of blood vessel narrowing after stent implantation. A drug eluting stent is a stent that has been coated with a drug, often in a polymeric carrier, that is known to interfere with the process of re-narrowing of the blood vessel (restenosis). Examples of various known drug eluting stents are disclosed in U.S. Pat. Nos. 5,649,977; 5,464,650; 5,591,227; 7,378,105; 7,445,792; 7,335,227, each of which are hereby incorporated by reference in their entirety. However, a drawback of drug eluting stents is a condition known as late stent thrombosis. This is an event where a blood clot forms inside the stent, which can occlude blood flow.

Drug coated balloons are believed to be a viable alternative to drug eluting stents in the treatment of atherosclerotic lesions. In a study which evaluated restenosis, and the rate of major adverse cardiac events such as heart attack, bypass, repeat stenosis, or death in patients treated with drug coated balloons and drug eluting stents, the patients treated with drug coated balloons experienced only 3.7% restenosis and 4.8% MACE (major adverse coronary events) as compared to patients treated with drug eluting stents, in which restenosis was 20.8% and 22.0% MACE rate. (See, PEPCAD II study, Rotenburg, Germany)

However, drug coated balloons present certain unique challenges. For example, the drug carried by the balloon needs to remain on the balloon during delivery to the lesion site, and released from the balloon surface to the blood vessel wall when the balloon is expanded inside the blood vessel. For coronary procedures, the balloon is typically inflated for less than one minute, typically about thirty seconds. The balloon inflation time may be longer for a peripheral procedure, however typically even for peripheral procedures the balloon is expanded for less than 5 minutes. Due to the short duration of contact between the drug coated balloon surface and the blood vessel wall, the balloon coating must exhibit efficient therapeutic agent transfer and/or efficient drug release during inflation. Thus, there are challenges specific to drug delivery via a drug coated or drug eluting balloon that are not present with a drug eluting stent.

Furthermore, conventional techniques for applying a coating, such as a therapeutic agent, may not be desirable for coating balloons, or other expandable members of medical devices. Such conventional techniques include spraying (air-atomization, ultrasonic, electrostatic, etc.), dip-coating, spin-coating, vapor deposition, roll coating, micro-droplet coating, etc. However, it is desirable to control the amount or dosage of therapeutic agent applied to the surface of the expandable member, and the location in which the therapeutic agent is applied. Many conventional techniques do not provide sufficient control over dosage, coating uniformity or edge control. Such control is further compromised when coating a medical device having a non-uniform configuration, such as a tapered balloon or a partially-inflated balloon, or when coating a medical device having a non-symmetrical surface, such as a balloon having a warped or bowed configuration. For example, peripheral balloons, being longer than coronary balloons, are more susceptible to warping or bowing along the longitudinal axis when inflated. Consequently, the amount and uniformity of coating applied to the balloon surface using conventional techniques may be compromised due to the non-uniform shape of the expandable member.

Thus there remains a need for, and an aim of the disclosed subject matter is directed toward, maintaining a fixed distance between the coating applicator and the surface of the expandable member during the application of one or more therapeutic agents thereto.

SUMMARY OF THE DISCLOSED SUBJECT MATTER

The purpose and advantages of the disclosed subject matter will be set forth in and are apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a system and method of coating an expandable member of a medical device. The system and corresponding method comprises providing an applicator in fluid communication with a fluid source, with the applicator having at least one outlet for applying fluid therefrom, and positioning the applicator proximate a surface of an expandable member. Relative movement is established between the at least one outlet and the surface of the expandable member along a coating path while maintaining a substantially fixed distance between the at least one outlet and the surface of the expandable member during relative movement therebetween. From the fixed distance, fluid is applied from the at least one outlet to form a controlled coating of fluid on the surface of the expandable member along the coating path.

The substantially fixed distance between the expandable member and the at least one outlet is maintained by determining the distance between a positioning device and the surface of the expandable member at a location, and displacing the at least one outlet to track the surface of the expandable member and employing a controller to adjust relative positioning of the at least one outlet and the surface of the expandable member. Particularly, maintaining the substantially fixed distance can include displacing the at least one outlet to track the surface of the expandable member.

The at least one outlet can be displaced relative to the surface of the expandable member. The positioning device can be in communication with a controller to generate a displacement command based upon the distance between the positioning device and the surface of the expandable member at the corresponding location. Further, the at least one outlet can be displaced according to the displacement command when the at least one outlet is aligned with the corresponding location. The determination of the distance between the positioning device and the surface of the expandable member can be performed over a length of the expandable member prior to applying fluid to the expandable member.

The positioning device can be embodied as a laser source configured to produce a beam directed towards the surface of the expandable member, or a sonar source configured to produce a pulse directed towards the surface of the expandable member. The controller processes the relationship between the positioning device and the surface of the expandable member to determine a displacement command wherein the at least one outlet is displaced according to that displacement command. Computation of the distance between the positioning device and the surface of the expandable member can be performed over a length of the expandable member prior to applying fluid to the expandable member. Alternatively, computation of the distance between the positioning device and the surface of the expandable member can be performed over a length of the expandable member during application of fluid to the expandable member.

According to another embodiment of the disclosed subject matter, a system for coating an expandable member of a medical device is provided. The system includes a support structure to support an expandable member of a medical device and an applicator in fluid communication with a fluid source. The applicator can have at least one outlet for applying fluid of the fluid source therefrom and the applicator can be positioned with the at least one outlet proximate a surface of an expandable member supported by the support structure. The system can also include a drive assembly to establish relative movement between the at least one outlet and the surface of the expandable member to apply fluid on the surface of the expandable member along a coating path and a positioning device to determine a distance to the surface of the expandable member at a corresponding location. A controller can maintain a substantially fixed distance between the at least one outlet and the surface of the expandable member when in alignment with the corresponding location. The controller can displace the at least one outlet to track the surface of the expandable member.

The controller can generate a displacement command to displace the at least one outlet of the applicator based upon the distance between the positioning device and the surface of the expandable member at the corresponding location. The at least one outlet can be disposed adjacent the positioning device. The positioning device can determine the distance between the positioning device and the surface of the expandable member over a length of the expandable member prior to applying fluid to the expandable member.

The positioning device is spaced from the surface of the expandable member, and the at least one outlet can be attached to a shuttle mechanism, such as a linear stage or the like. The positioning device can include a laser source configured to produce a beam directed towards the surface of the expandable member. In another embodiment, the positioning device can include a sonar source configured to produce a pulse directed towards the surface of the expandable member.

In operation, the shuttle mechanism is displaced generally perpendicularly to a longitudinal axis of the expandable member. The shuttle mechanism can be displaced upon receipt of the displacement command from the controller. Further, the at least one outlet can be disposed adjacent the positioning device. The shuttle mechanism can be moved according to the displacement command from the controller. The expandable member can be at least partially expanded prior to dispensing fluid to the surface of the expandable member.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

DETAILED DESCRIPTION

Reference will now be made in detail to embodiments of the disclosed subject matter, an example of which is illustrated in the accompanying drawing. The method and corresponding steps of the disclosed subject matter will be described in conjunction with the detailed description of the system.

The methods and systems presented herein can be used for applying one or more coatings to a medical device. The disclosed subject matter is particularly suited for applying a uniform coating of therapeutic agents, and other fluid compounds, to select portions of an expandable member. While the disclosed subject matter references application of a fluid to an expandable member, it is to be understood that the methods and systems disclosed herein can also be employed to apply therapeutic, polymeric, or matrix coatings to various surfaces of medical devices, as so desired.

The disclosed subject matter provides a method, and corresponding system, to coat an expandable member, or select portions thereof, by a variety of application processes while maintaining a substantially fixed distance between the outlet of the applicator and the surface of the expandable member.

In accordance with the disclosed subject matter, a system and corresponding method of coating an expandable member of a medical device comprises providing an applicator in fluid communication with a fluid source, with the applicator having at least one outlet for applying fluid therefrom, and positioning the applicator proximate a surface of an expandable member. Relative movement is established between the at least one outlet and the surface of the expandable member along a coating path while maintaining a substantially fixed distance between the at least one outlet and the surface of the expandable member during relative movement therebetween, wherein maintaining the substantially fixed distance includes displacing the at least one outlet to track the surface of the expandable member. From the fixed distance, fluid is applied from the at least one outlet to form a coating of fluid on the surface of the expandable member along the coating path.

Figure 1:
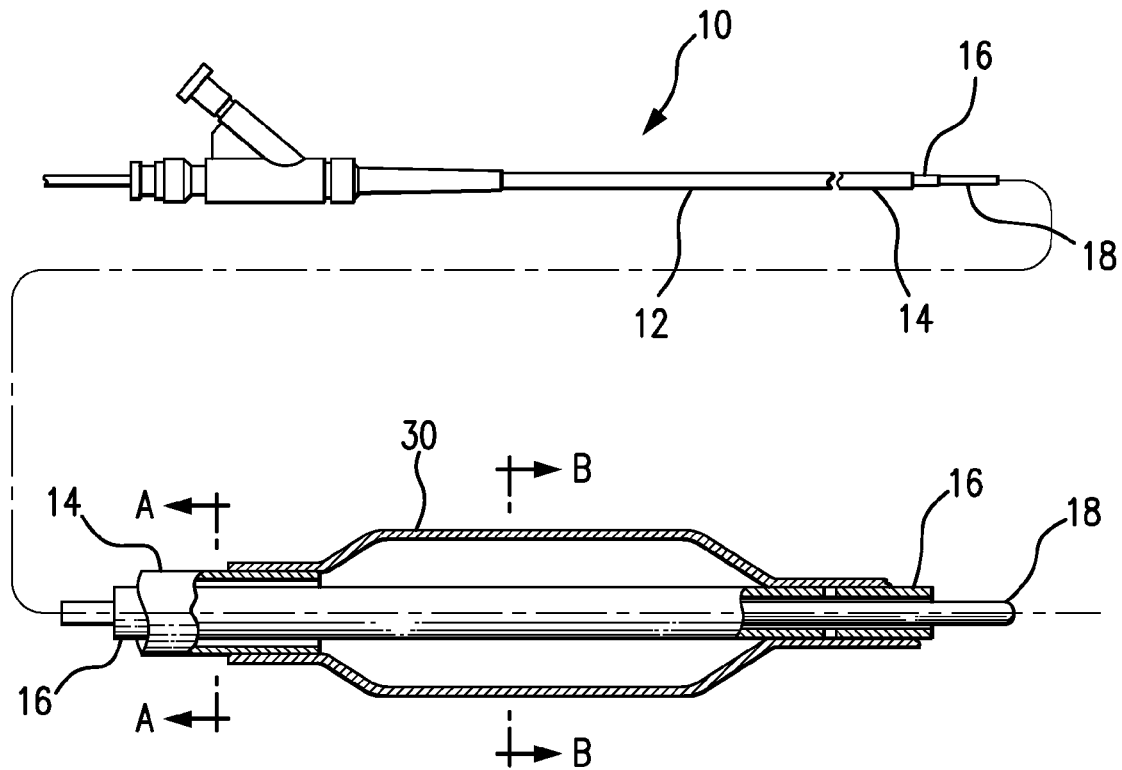
FIG. 1 is a schematic side view in partial cross-section of a representative balloon catheter in accordance with the disclosed subject matter.
Figures 1A, 1B:
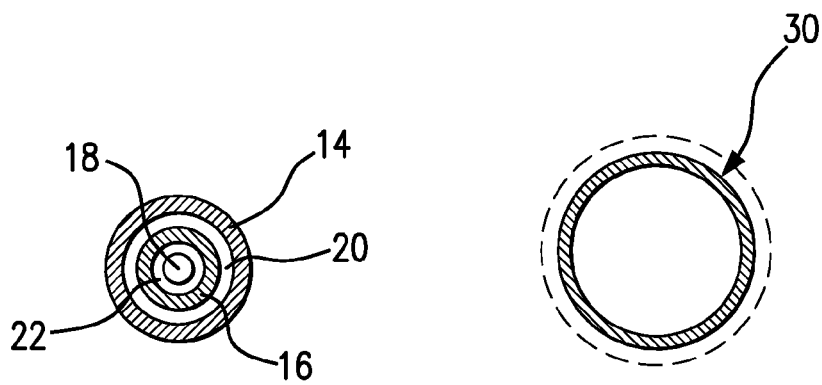
FIG. 1A is a cross-sectional view taken along lines A-A in FIG. 1.
FIG. 1B is a cross-sectional view taken along lines B-B in FIG. 1.

For purpose of explanation and illustration, and not limitation, an exemplary embodiment of a medical device having an expandable member is shown schematically in FIGS. 1 and 1A. Particularly, and as illustrated, the medical device embodied herein is a balloon catheter 10, which includes an elongated catheter shaft 12 having a proximal end and having a distal end and an expandable member 30 located proximate the distal end of the catheter shaft. The expandable member, or balloon as depicted herein for purpose of illustration and not limitation, has an outer surface and an inner surface disposed at the distal end portion of the catheter shaft. In accordance with the disclosed subject matter, a coating is applied to at least a portion of the outer surface of the balloon.

The elongated catheter shaft 12 comprises an outer tubular member 14 and an inner tubular member 16. The outer tubular member 14 defines an inflation lumen 20 disposed between the proximal end portion and the distal end portion of the catheter shaft 12. Specifically, as illustrated in FIG. 1A, the coaxial relationship of this representative embodiment defines an annular inflation lumen 20 between the inner tubular member 16 and the outer tubular member 14. The expandable member 30 is in fluid communication with the inflation lumen 20. The inflation lumen can supply an inflation medium under positive pressure and can withdraw the infla-tion medium, i.e. provide negative pressure, from the expandable member. The expandable member 30 can thus be inflated and deflated. The elongated catheter is sized and configured for delivery through a tortuous anatomy, and can further include a guidewire lumen 22 that permits it to be delivered over a guidewire 18. As illustrated in FIG. 1A, the inner tubular member 16 defines the guidewire lumen 22 for the guidewire 18. Although FIGS. 1 and 1B illustrate the guidewire lumen formed as a separate inner member having an over-the-wire (OTW) construction, the guidewire lumen can be formed of a dual lumen member with either an over-the-wire (OTW) or a rapid-exchange (RX) construction, as is well known in the art.

A wide variety of balloon catheters and expandable members constructions are known and suitable for use in accordance with the disclosed subject matter. For example, the expandable member can be made from polymeric material such as compliant, non-compliant or semi-compliant polymeric material or polymeric blends. Examples of such suitable materials include, but are not limited to, nylon 12, nylon 11, nylon 9, nylon 6, nylon 6/12, nylon 6/11, nylon 6/9, and nylon 6/6, polyurethane, silicone-polyurethane, polyesters, polyester copolymers, and polyethylene. Examples of other balloon and catheter embodiments which can be employed in accordance with the disclosed subject matter include U.S. Pat. Nos. 4,748,982; 5,496,346; 5,626,600; 5,300,085, 6,406,457 and application Ser. Nos. 12/371,426; 11/539,944; 12/371,422, each of which is hereby incorporated by reference in its entirety.

In one embodiment, the coating is applied to the expandable member of the fully assembled medical device. As described above with reference to FIGS. 1A-B, medical devices such as the catheter 10 include a plurality of components which are typically manufactured as separate discrete components and thereafter assembled together. Applying a coating to the expandable member at an upstream stage of an assembly line can require extensive measures to minimize or prevent the coating from being exposed to various equipment and processes during the downstream stages of the assembly line. Such exposure can render the coating prone to damage and/or contamination during final assembly of the catheter, and can result in scrapping of the entire catheter. Similarly, coating of the expandable member prior to assembly of the catheter can result in contamination of equipment in the assembly line if appropriate measures are not taken. In order to avoid such damage and exposure in conventional catheter assembly lines, additional equipment including monitoring and safety controls would be required. Accordingly, applying the coating to the expandable member after assembly of the catheter, as disclosed herein, avoids the unnecessary complexity and excessive costs associated with a modified assembly line.

In accordance with the disclosed subject matter, any of a variety of fluid compositions can be applied to the expandable member. For example, the fluid can include a therapeutic agent for treatment of a disease state. Examples of suitable therapeutic agents include anti-proliferative, anti-inflammatory, antineoplastic, antiplatelet, anti-coagulant, anti-fibrin, antithrombotic, antimitotic, antibiotic, antiallergic and antioxidant compounds. Such therapeutic agents can be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent including streptokinase and tissue plasminogen activator, an antigen, a hormone, a growth factor, a ribozyme, and a retroviral vector.

As embodied herein, for purpose of illustration, the therapeutic agents include a cytostatic drug. The term "cytostatic" as used herein means a drug that mitigates cell proliferation but allows cell migration. These cytostatic drugs include for the purpose of illustration and without limitation, macrolide antibiotics, rapamycin, everolimus, zotarolimus, biolimus, temsirolimus, deforolimus, novolimus, myolimus, structural derivatives and functional analogues of rapamycin, structural derivatives and functional analogues of everolimus, structural derivatives and functional analogues of zotarolimus and any marcrolide immunosuppressive drugs. The term "cytotoxic" as used herein means a drug used to inhibit cell growth, such as chemotherapeutic drugs. Some non-limiting examples of cytotoxic drugs include vincristine, actinomycin, cisplatin, taxanes, paclitaxel, and protaxel.

Additionally or alternatively, the fluid can include other compounds or additives, such as polymers, binding agents, plasticizers, solvents, surfactants, additives, chelators, fillers, and the like. An exemplary formulation of the disclosed subject matter includes zotarolimus, polyvinylpyrrolidone and glycerol. In one embodiment the therapeutic agent can be provided in liquid form or dissolved in a suitable solvent. In another embodiment, the therapeutic agent is provided as a particulate and mixed in a suitable carrier for application as a fluid.

In accordance with an aspect of the disclosed subject matter, a variety of techniques for applying a coating of therapeutic agent can be employed, such as spraying (air-atomization, ultrasonic, electrostatic, etc.), vapor deposition, microdroplet coating, etc. Additionally or alternatively, a direct coating process can be used, and is embodied herein, as further disclosed in U.S. Pat. No. 7,455,876 and U.S. Patent Application Publication No. 2010/0055294, the entirety of each is hereby incorporated by reference, can be employed in accordance with the disclosed subject matter. For purpose of illustration and not limitation, reference will be made to a direct coating process, although the disclosed subject matter is equally applicable to other suitable coating application techniques.

Figure 2:
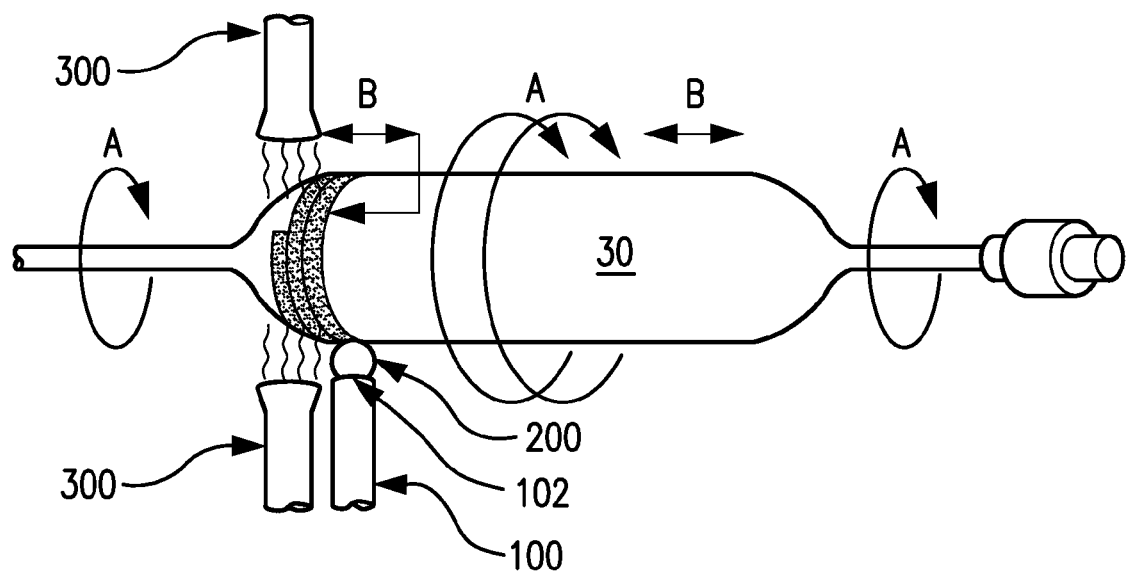
FIG. 2 is a schematic view of an applicator assembly for direct fluid coating on the surface of an expandable member.

An exemplary embodiment of the direct coating process and system is illustrated in FIG. 2 for purpose of explanation and not limitation. The applicator depicted herein is shown as a pipette 100 having an outlet 102 positioned proximate expandable member 30 such that the fluid 200 dispensed from the pipette is deposited on the surface of the expandable member. FIG. 2 depicts the pipette 100 generally normal or at a right angle to the balloon surface. However, alternative alignments and orientations can be used as desired or needed for the type and dimensions of expandable members.

Coating process and systems of the disclosed subject matter can be performed with the expandable member in a partially or fully inflated condition, or in a deflated condition if desired. If deflated, the expandable member can have a generally smooth exposed surface if made of a compliant material, or can be pleated, folded, wrinkled or pressed if made of a semi-compliant or non-compliant material. For purpose of illustration, FIG. 2 shows the expandable member 30 in an inflated condition to allow coating of all or select portions of the outer surface. Additionally, the temperature of the expansion medium, or the expandable member itself, can be controlled to further maintain or define the contour of the expandable member.

As fluid is delivered from the applicator or pipette 100, relative movement is established between the applicator 100 and the expandable member 30 to effect a continuous or patterned coating path as desired. For example, and as depicted in FIG. 2, the coating path can define a generally continuous spiral or helical pattern along the outer surface of the expandable member. Alternatively, coating paths can be established as discrete circumferential rings, discrete lines extending along the expandable members longitudinal axis, or combinations or portions thereof.

The relative movement can include rotation, translation, or combinations thereof, of either, or both, the expandable member and the applicator. For example, the expandable member 30 can be rotated about its central axis, as shown by arrows A in FIG. 2, and simultaneously translated along the central axis, as shown by arrow B in FIG. 2. Additionally, or alternatively the expandable member 30 can rotate relative a first axis, and the applicator 100 translate relative the axis, e.g., to define a helical coating path. Accordingly, any number of coating paths can be selected and provided on the expandable member. The various movements described herein can be performed simultaneously, sequentially, continuously or intermittently, as so desired. As embodied herein, the expandable member can be rotated at speeds between about 5 and 1000 rpm, depending upon the coating fluid and related parameters during coating, and translated relative to the applicator at speeds between about 0.02 and 10 cm/sec.

The desired portions or areas of the expandable member can be coated with a single pass or cycle of relative movement between the expandable member and applicator. Alternatively, a plurality of passes or cycles of coating operation can be performed. Such multiple passes or cycles allow for further variation in the coating properties along the expandable member length or select areas. For example, one portion of the expandable member can be coated with a different number of coating layers of fluid than another portion of the expandable member thereby creating a gradient of the coating on the expandable member. Further, various layers of different coating formulations can be applied to the expandable member using the method and system disclosed herein. For example, one or more layers of therapeutic-free primers, concentrated therapeutic layers, drug-excipient layers, and/or release control layers can be applied. These varied coating properties allow for greater flexibility and customization of the catheter to provide a greater range of applications and uses.

In accordance with another aspect of the disclosed subject matter, drying can be employed to accelerate the coating process, such as by applying heat, forced gas, cooled gas, vacuum, infra-red energy, microwave energy, or a combination thereof to the coated surface of the expandable member. With regard to a direct coating operation, for purpose of illustration and not limitation, FIG. 2 shows a dryer 300 can be provided upstream of or adjacent to the applicator for drying concurrent with or shortly after coating application. In one embodiment, the drying nozzle can be collinear with the applicator by circumscribing or surrounding the applicator with an annular opening. Additionally or alternatively, drying can be conducted between successive coating passes or cycles. The dryer 300 can be oriented at any suitable angle relative to the surface of the expandable member, and can be configured for relative movement with or independent of the applicator relative to the expandable member.

While the direct coating applicator of the embodiment illustrated in FIG. 2 is depicted as a pipette, additional or alternative applicators can be employed. Some examples of suitable direct coating applicators include flexible tubing, coaxial tubing, hypotubes, dies, ball-bearing dispense tubing, syringe, needles, brushes, sponges, cones and foam applicators. Furthermore, FIG. 2 depicts a direct coating applicator having a single outlet 102, a plurality of outlets can be employed if desired. The outlets can be disposed adjacent each other along the axis of the expandable member, and/or spaced circumferentially about the expandable member. In this regard, one or more of a plurality of reservoirs containing the same or different coating solutions can be provided in fluid communication with each outlet of the applicator, respectively. As with the outlet of FIG. 2, each outlet of the applicator can be positioned at various locations and orientations relative to the surface of the expandable member. Additionally, the expandable member 30 can be oriented in a generally horizontal position, as shown in FIG. 2, vertically, or at or at any angle between as suitable. For example, arranging the expandable member for a vertical configuration can be advantageous in larger size expandable members, e.g. peripheral balloons, to allow gravitational force to act parallel with the longitudinal axis of the expandable member to reduce deformation of the expandable member and associated catheter shaft.

Movement of the medical device and/or the outlet of the applicator is accomplished by providing a support assembly. The support assembly can maintain the position of one element, e.g. the applicator, while allowing movement of the other element, e.g., the medical device. Alternatively, the support assembly can allow movement of both elements. Movement can be performed manually, or by providing a drive assembly with suitable drive source, such as a motor or the like, and appropriate controller as know in the art.

In accordance with the disclosed subject matter, the applicator is maintained at a predetermined or fixed distance from the expandable member surface. Maintaining a fixed distance between the outlet of the applicator and the expandable member, in combination with rotation and translation as discussed above, provides greater control over the coating pattern to be applied to the expandable member surface. Such control provides a consistent and uniform dosage of the therapeutic agent along the surface of the expandable member, resulting in a coating with increased efficacy and good content uniformity. Additionally, maintaining a fixed distance allows greater control for coating an expandable member at discrete locations, if desired, or with non-uniform patterns, such as to create varied local areal density along selected portions of the expandable member.

Furthermore, maintaining a fixed distance between the outlet of the applicator and the expandable member surface reduces the amount of waste or excess coating which is not retained on the expandable member. For example, with spray coating techniques, the amount of waste or excess coating generally increases with the distance between the outlet(s) and the surface of the expandable member. Conversely, if the distance between the outlet of the applicator and the expandable member surface are too small, undesired or accidental contact between the outlet of the applicator and expandable member surface can occur resulting in tearing or scratching of the expandable member surface, abrasion to the coating applied to the expandable member, or bare spots in the coating. The distance between the outlet and the surface of the expandable member can depend upon a number of variables, including viscosity of the fluid, surface tension of the fluid, pump rate of the fluid, diameter of the applicator exit orifice, volatility of the solvents in the fluid, speed at which the fluid is dispensed, diameter or shape of the expandable member, and/or size of the outlet opening. For example, when using a pipette type applicator for direct coating applications, the distance between the outlet and the surface generally should be less than 40 times the smallest cross dimension of the outlet.

As disclosed herein, the fixed distance between the at least one outlet of the applicator and the surface of the expandable member is maintained by determining a distance between a positioning device and the surface of the expandable member at a corresponding location, and displacing the position of the at least one outlet relative to the surface of the expandable member when aligned with the corresponding location. The substantially fixed distance can be maintained by displacing the at least one outlet of the applicator, or by displacing the expandable member relative to the at least one outlet.

The positioning device generally includes an energy source to emit energy toward the surface of the expandable member and a sensor or receiver to measure the energy after impacting the expandable member surface. For example, the positioning device can include a laser source configured to produce a beam directed towards a location on the surface of the expandable member, or a sonar source configured to produce a pulse directed towards a location on the surface of the expandable member. The change in energy after impacting the expandable member surface, e.g., the reflected energy, is measured and processed to determine the distance or relationship from the known location of the positioning device to the expandable member surface at the corresponding location. Based upon this distance, a controller can then generate a displacement command for displacement of the at least one outlet when in alignment with the corresponding location along the expandable member surface, as needed, to maintain the desired fixed distance therebetween.

Determination of the distance between the positioning device and the surface of the expandable member can be performed at corresponding locations over the entire length or only a portion of the expandable member prior to applying the coating. Alternatively, determination of the distance between the positioning device and the surface of the expandable member can be performed substantially simultaneously during application of the coating to the expandable member. Such a technique is generally suitable for any of a variety of known expandable members, including conventional cylindrical balloons, as well as tapered, shaped and stepped balloons or the like. By tracking the surface of the expandable member, the various coating techniques can adjust for minor distortions or features—whether intentional or unintentional—in the surface of the expandable member. Furthermore, and as described further below, the method and system of the disclosed subject matter also is suitable for use with bowed or warped balloons, such as peripheral balloons that due to their longer lengths can have greater distortions.

In accordance with another aspect of the disclosed subject matter, the tracking mechanism can be configured for displacement of the applicator outlet in at least one direction in a plane generally orthogonal to the longitudinal axis in which the expandable member is supported. This aspect is particularly beneficial for use with an expandable member having a distorted or asymmetric configuration along its longitudinal axis, such as a bowed or warped balloon. For example, an expandable member of significant length, such as a peripheral balloon, can tend to bow or warp and thus result in an asymmetric shape. Likewise, distorted configurations can result from the particular material properties used for the expandable member, as well as the various manufacturing processes performed e.g., blowing, stretching, shrinking, welding, etc.

Figure 3A:
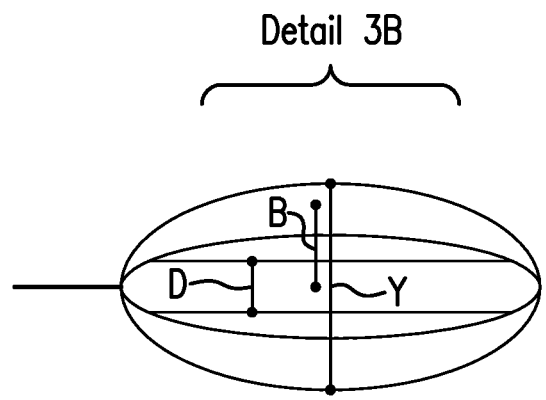
FIGS. 3A and 3B are a schematic representation and an enlarged detail section, respectively, of an expandable member having a bowed configuration relative to a true symmetrical expandable member along a common longitudinal axis.
Figure 3B:
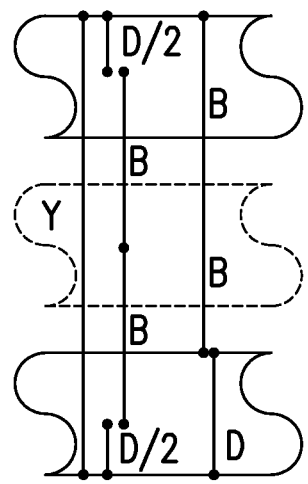

For purpose of explanation, one example of a quantitative measurement of the amount of asymmetry of an expandable member is depicted in FIGS. 3A and 3B. Particularly, FIG. 3A schematically depicts the distortion of a bowed balloon during rotation relative to a true symmetrical expandable member. FIG. 3B is an enlarged detail view of the schematic depiction of FIG. 3A to demonstrate certain relevant dimensions. As depicted, the amount of bowing of the expandable member is defined by the formula $B=(Y-D)/2$, wherein B is defined as the amount of bowing from a true longitudinal axis; D is defined as the diameter of the expandable member; and Y is defined as the distance from a surface of the expandable member with respect to the true longitudinal axis. Accordingly, for an expandable member, which is symmetrical about a central axis, the value of B is equal to zero.

Figure 4A:
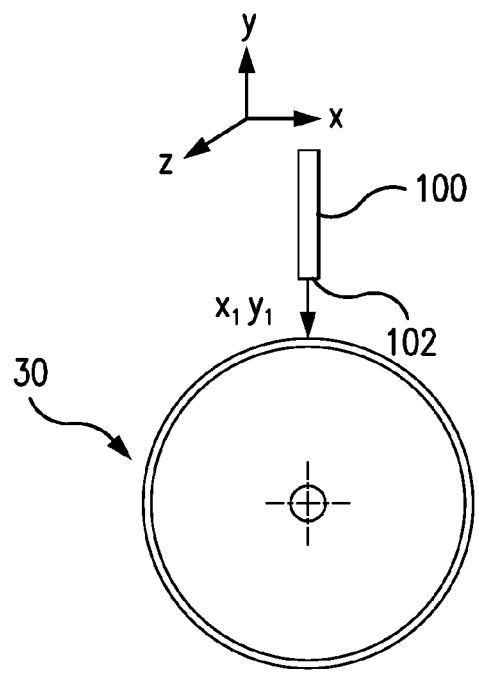
FIGS. 4A and 4B are schematic cross-sectional views of the spaced relationship between an applicator and an expandable member without and with a bowed configuration, respectively.
Figure 4B:
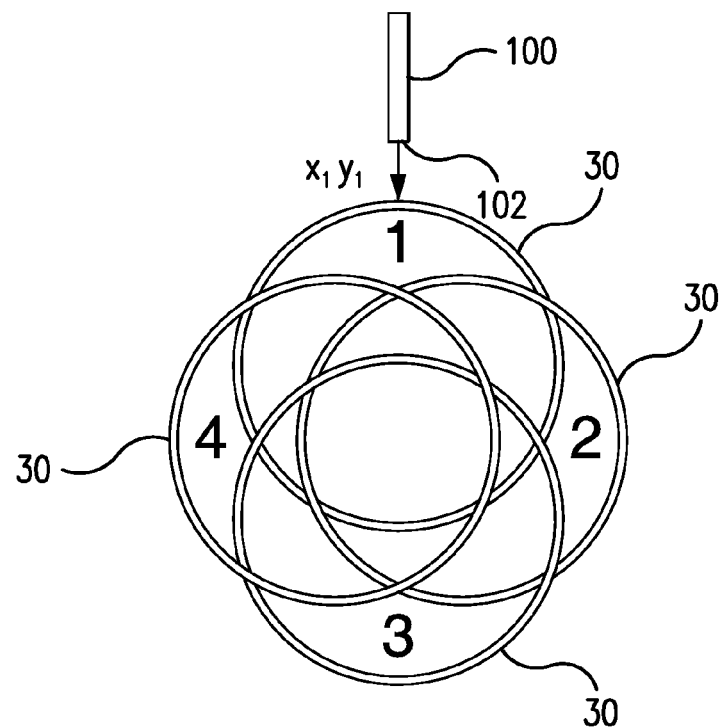

FIG. 4A illustrates a cross-sectional view of a true symmetrical expandable member. As shown in FIG. 4A, as the expandable member is rotated about its central axis, the distance from the applicator outlet to the top center of the balloon remains fixed at a constant position, indicated by coordinates $X_1Y_1$. Accordingly, the applicator outlet can remain in a single and fixed position with the distance between the applicator and the expandable member remaining constant. By contrast, FIG. 4B depicts four (1-4) positions of rotation of an asymmetrical expandable member relative to an applicator outlet maintained in a fixed position. When the asymmetrical expandable member is rotated about its central axis, as illustrated in FIG. 4B, the distance between the fixed applicator outlet and the top center of the rotating expandable member (i.e., $X_1Y_1$ in position 1) will vary in both the X axis and the Y axis—and thus result in a non-uniform coating. For purpose of illustration, the amount of bowing is exaggerated to demonstrate the amount of potential offset from the outlet of an applicator maintained at a fixed location.

Therefore, and in accordance with the disclosed subject matter, the distance between the outlet of the applicator and the surface of the expandable member can be monitored and maintained in a number of ways. For example, and as disclosed herein for purpose of illustration and not limitation, the fixed distance can be maintained between the outlet of the applicator and the expandable member surface by employing a positioning device to monitor the surface contour of the expandable member and a controller to adjust the relative position of the outlet of the applicator, such as by displacing the outlet or by displacing the expandable member.

Figure 5:
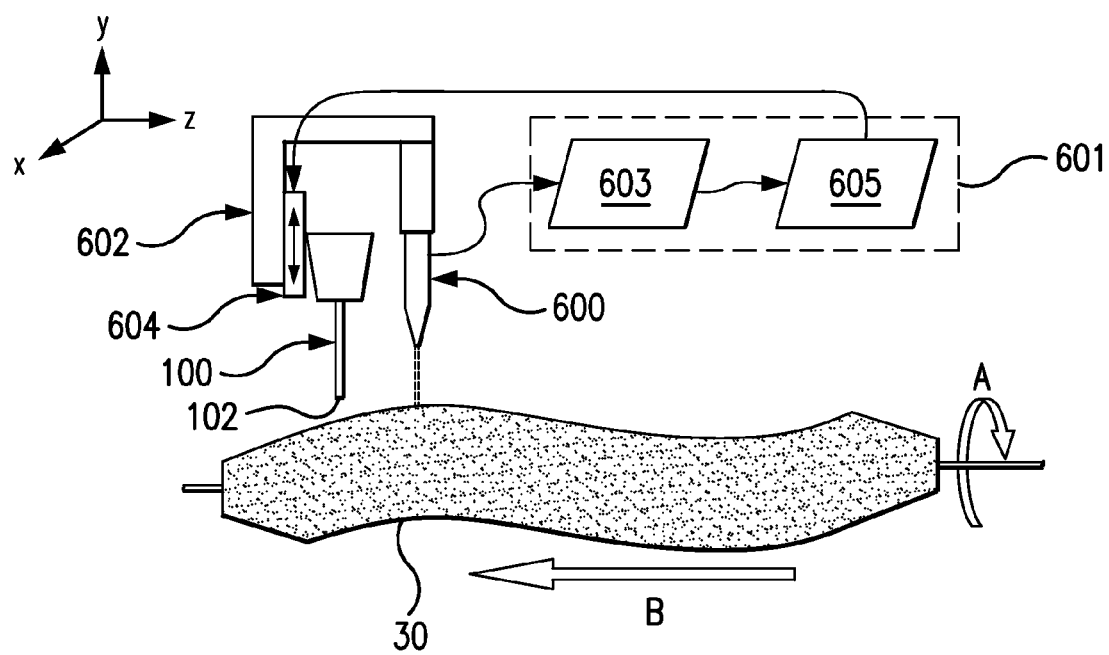
FIG. 5 is a schematic representation of an expandable member and coating system with a position measurement system in accordance with the disclosed subject matter.

For purpose of illustration, and not limitation, FIG. 5 provides a schematic representation of the coating system and positioning device in accordance with the disclosed subject matter. As shown in FIG. 5, the positioning device 600 can include a laser or sonar pulse source in communication with a data processor 603 to measure the varying distance from the positioning device or source 600 to the surface of the expandable member 30 without physical contact therebetween. Laser positioning devices perform precise measurements at a relatively low cost. Sonar positioning devices are used in applications involving transparent expandable members wherein a laser beam does not adequately reflect off of the surface of the expandable member. The data obtained from the laser or sonar positioning device is processed to determine the distance or relationship between the positioning device 600, which is fixed at a known height or location, and a corresponding point or location along the surface of the expandable member 30, i.e., the location on the expandable member surface at which the beam or pulse impacts or is reflected. Based on this distance, a command can be generated by controller 605 to displace the position of the applicator outlet 102 relative to the surface of the expandable member 30 to maintain the desired fixed distance therebetween when the applicator outlet 102 is aligned with the corresponding location along the surface of the expandable member 30. The determination of distance and generation of displacement command can be performed continuously or updated intermittently as desired. Likewise, determination of the distance between the positioning device and the surface of the expandable member can be performed in advance of the coating process, such as to map the surface of the expandable member for subsequent control of the coating process, or can be performed substantially simultaneously with the coating process for real time control. The data processor and controller can be provided as separate components or as a single computer as embodied herein.

As further embodied herein, the positioning device 600 and applicator are configured to translate relative to the expandable member, e.g., translate along and relative to the longitudinal axis of the expandable member. For example, and as illustrated in FIG. 5, the positioning device 600 is rigidly attached to a bracket member 602 that is generally fixed in the Y direction but that can translate relative to the expandable member in the Z direction as shown. The applicator 100, or at least the outlet 102 of the applicator, is mounted to the bracket member 602 by a shuttle mechanism, e.g., a linear stage 604, for displacement in the Y direction relative to the positioning device 600 as shown in FIG. 5. The applicator outlet 102 therefore can be displaced in the Y direction during the coating process in response to the displacement command from the controller. Alternatively, the bracket member as a whole and/or the expandable member can be configured to adjust or displace in the Y direction to adjust or displace the position of the applicator outlet 102 relative the surface of the expandable member 30. Such a configuration can be used, for example, if the positioning device is used to map the surface contour of the expandable member prior to the coating process.

Based on the known location of the of positioning device and the distance to the expandable member surface, as well as the known relationship between the positioning device and the applicator outlet (e.g. spray nozzle, pipette, etc.), as well as rotational speed and linear speed of the expandable member, the applicator outlet can be adjusted or displaced to apply a controlled and uniform coating over the desired length or area of the expandable member. That is, the position of the applicator outlet is adjusted to compensate for varying surface contour of the expandable member and to maintain a fixed distance therebetween. Further, the predetermined fixed distance between the applicator outlet and the expandable member surface can be selectively altered as needed to accommodate various sizes of expandable members, as well as various sizes or types of applicators.

In operation, and with reference to the representative embodiment of FIG. 5 for purpose of illustration and not limitation, the positioning device 600 transmits energy, e.g., laser beam or sonar pulse to corresponding locations along the expandable member surface, and measures the resulting energy to determine the distance from the positioning device to the expandable member surface. The data processor 603 is calibrated or otherwise provided with the relationship between the positioning device 600 and the outlet 102 of the applicator 100. Based upon the signal response from the positioning device 600, the computer 601 determines the relative relationship between the surface of the expandable member 30, the positioning device 600 and the applicator outlet 102 and generates displacement commands required to maintain the desired fixed distance as the applicator outlet is aligned with the corresponding locations along the expandable member, e.g., by actuating the linear stage 604. Additionally, this information, including the distances, relationships and amount of fluid applied at the corresponding locations along the surface of the expandable member, among other things, can be stored for future records and use as desired.

The positioning device can be employed substantially concurrently with the coating process described above. In this regard, the positioning device is generally operated in a real-time manner to determine the surface contour of the expandable member and displace the applicator outlet accordingly in order to track or maintain the desired fixed distance. Alternatively, and as previously noted, the positioning device can be operated in advance of the coating process to map the desired surface of the expandable member based upon one or more reference points. The corresponding measurements of the surface contour are stored and relied upon during the coating process using a series of pre-determined commands generated by the computer or controller to displace the applicator. An example of a suitable laser scanning system and technology to read and generate displacement commands in accordance with the method and system as disclosed herein, has been used in the pharmaceutical drug screening field. Particularly, fluorescence plate readers are known for reading and measuring high density assay plates. This system uses a laser to scan the bottom of the plate prior to fluorescence reading to compensate for small differences or warping of the plate. The data from the scan is then used to position the optical head appropriately during fluorescence reading such that the distance between the optical head and the plate surface remain fixed throughout the screening process. This similar technology can be modified according by one skilled in the art for use in the method and system disclosed herein.

By utilizing a positioning device that does not contact the surface of the expandable member, the risk of interfering or disturbing the coating dispensed from the outlet can be minimized. Additionally, the absence of contact between the expandable member and the positioning device is advantageous in reducing the forces required to establish the relative movement between the expandable member and the outlet of the applicator. As previously noted, the coating method and system of the disclosed subject matter can be performed on a fully assembled medical device, e.g. balloon catheters, wherein the force required to rotate or otherwise move the expandable member is applied to the medical device at a location remote of the expandable member. Therefore, significant force may be required to overcome the friction and inertia of the various components of the medical device in order to achieve movement of the expandable member. Thus, the reduction or minimization of contact with the expandable member is advantageous as the frictional forces generated during the relative movement will in turn be minimized, thereby reducing the amount of force required by the support assembly, or manual operator, to establish relative movement. Furthermore, the various components of a medical device such as a balloon catheter are not torsionally rigid. Therefore undue friction on the expandable member can lead to torsional loading and unloading of the proximal members. This can lead to inconsistent rotation of the medical device, and thus non-uniform coating.

If desired, a protective sheath can be provided to protect the coating during shipping and storage and/or during delivery of the coated expandable member through the body lumen. A variety of sheaths are known, including removable sheaths or balloon covers, retractable sheaths to be withdrawn prior to deployment of the balloon, and elastic sheaths that conform to the balloon upon expansion. Such elastic sheaths can be porous or include apertures along a portion thereof. In operation, the inflation of the expandable member causes the sheath to expand for release of the coating and/or therapeutic agent through the porous wall or apertures to the tissue of the arterial wall. For example, see U.S. Pat. No. 5,370,614 to Amundson, the disclosure of which is incorporated by reference in its entirety.

In accordance with in the disclosed subject matter, an endoprosthesis, e.g. stent, can be mounted on the expandable member. The type of stent that can be used includes, but is not limited to, bare metal stent, drug eluting stent, bioabsorbable stent, balloon-expandable stent, self-expanding stent, prohealing stent, and self-expanding vulnerable plaque implant. The expandable member can be coated independently of the stent or in conjunction with the stent coating process. The stent coating can contain the same or different therapeutic agents from the catheter or expandable member. However, the particular coating on the catheter or expandable member can have distinct release kinetics from the therapeutic coating on the stent. The coating applied to the expandable member can be allowed to dry prior to placement of the stent thereon.

Alternatively, the endoprosthesis can be positioned and/or crimped on to the expandable member before the coating is allowed to dry or cure past a "tacky" state. This would enable adhesion of the coating between the expandable member and the endoprosthesis. This process increases the retention of the prosthesis onto the expandable member (acting as an endoprosthesis retention enhancer) thus reducing the risk of dislodgement of the endoprosthesis during the torturous delivery through the vascular lumen While the disclosed subject matter is described herein in terms of certain example embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A method of coating a balloon of a medical device, comprising:

rotatably supporting a balloon of a medical device on a support structure;

providing an applicator in fluid communication with a fluid source, the applicator having at least one outlet for applying fluid therefrom;

positioning the at least one outlet of the applicator proximate a surface of the balloon;

establishing relative movement between the at least one outlet and the surface of the balloon along a coating path;

determining a distance between a positioning device and the surface of the balloon at a corresponding location in real-time thereby maintaining a substantially fixed distance between the at least one outlet and the surface of the balloon at the corresponding location; and applying fluid from the at least one outlet to form a direct coating of fluid on the surface of the balloon along the coating path.

2. The method of claim 1, wherein maintaining the substantially fixed distance includes displacing the surface of the balloon relative to the at least one outlet.

3. The method of claim 1, wherein the positioning device includes a laser source configured to produce a beam directed towards the surface of the balloon.

4. The method of claim 1, wherein the positioning device includes a sonar source configured to produce a pulse directed towards the surface of the balloon.

5. The method of claim 1, wherein maintaining the substantially fixed distance includes displacing the at least one outlet relative to the surface of the balloon.

6. The method of claim 5, wherein the positioning device is in communication with a controller to generate a displacement command based upon the distance between the positioning device and the surface of the balloon at the corresponding location.

7. The method of claim 6, wherein the at least one outlet is displaced according to the displacement command when the at least one outlet is aligned with the corresponding location.

8. The method of claim 1, wherein the at least one outlet is disposed adjacent the positioning device.

9. The method of claim 1, wherein determining the distance between the positioning device and the surface of the balloon is performed over a length of the balloon prior to applying fluid to the balloon.

10. A system for coating a balloon of a medical device, the system comprising:
a support structure to rotatably support a balloon of a medical device;
an applicator in fluid communication with a fluid source, the applicator having at least one outlet for applying fluid of the fluid source therefrom to form a direct coating of fluid on the surface of the balloon along a coating path, the applicator positioned with the at least one outlet proximate a surface of the balloon;
a drive assembly to establish relative movement between the at least one outlet and the surface of the balloon to apply fluid on the surface of the balloon along the coating path; and
a positioning device to determine a distance to the surface of the balloon at a corresponding location in real-time; and
a controller configured to maintain a substantially fixed distance between the at least one outlet and the surface of the balloon when in alignment with the corresponding location.

11. The system of claim 10, wherein the controller displaces the at least one outlet to track the surface of the balloon.

12. The system of claim 10, wherein the positioning device is spaced from the surface of the balloon.

13. The system of claim 10, wherein the positioning device includes a laser source configured to produce a beam directed towards the surface of the balloon.

14. The system of claim 10, wherein the positioning device includes a sonar source configured to produce a pulse directed towards the surface of the balloon.

15. The system of claim 10, wherein the controller generates a displacement command to displace the at least one outlet of the applicator based upon the distance between the positioning device and the surface of the balloon at the corresponding location.

16. The system of claim 15, wherein the at least one outlet is fixedly attached to a shuttle mechanism.

17. The system of claim 16, wherein the shuttle mechanism is moved according to the displacement command from the controller.

18. The system of claim 17, wherein the shuttle mechanism is displaced generally perpendicularly to a longitudinal axis of the balloon.

19. The system of claim 10, wherein the at least one outlet is disposed adjacent the positioning device.

20. The system of claim 10, wherein the positioning device determines the distance between the positioning device and the surface of the balloon over a length of the balloon prior to applying fluid to the balloon.

21. The system of claim 10, further comprising an inflation device to inflate the balloon.

22. The system of claim 10, wherein the applicator consists of two degrees of movement.

23. The system of claim 10, wherein the controller dynamically moves the applicator relative to the support structure.

24. The system of claim 10, the coating path comprises a continuous coating path delivered from the at least one outlet.

* * * * *